US012681001B2

(12) United States Patent
Gisolf et al.

(10) Patent No.: US 12,681,001 B2
(45) Date of Patent: Jul. 14, 2026

(54) DEEP TRANSIENT TESTING (DTT) DOWNHOLE AND SURFACE GAS RATE INTEGRATION WORKFLOW

(71) Applicant: Schlumberger Technology Corporation, Sugar Land, TX (US)

(72) Inventors: Adriaan Gerard Gisolf, Bucharest (RO); Bertrand Claude Emile Theuveny, Paris (FR); Francois Xavier Dubost, Paris (FR); Bei Gao, Shenzhen (CN); Maneesh Pisharat, Bucharest (RO); Ivan Fornasier, Paris (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 187 days.

(21) Appl. No.: 18/764,515

(22) Filed: Jul. 5, 2024

(65) Prior Publication Data

US 2025/0012776 A1      Jan. 9, 2025

Related U.S. Application Data

(60) Provisional application No. 63/512,107, filed on Jul. 6, 2023.

(51) Int. Cl.
*G01N 33/28* (2006.01)
*E21B 21/06* (2006.01)
(Continued)

(52) U.S. Cl.
CPC ....... *G01N 33/2823* (2013.01); *E21B 21/067* (2013.01); *E21B 21/08* (2013.01); *G01N 9/00* (2013.01); *E21B 2200/20* (2020.05)

(58) Field of Classification Search
None
See application file for complete search history.

(56) References Cited

U.S. PATENT DOCUMENTS

| | | |
|---|---|---|
| 5,424,959 A | 6/1995 | Reyes |
| 7,081,615 B2 | 7/2006 | Betancourt |
| (Continued) | | |

FOREIGN PATENT DOCUMENTS

| | | |
|---|---|---|
| EP | 3685004 A1 | 7/2020 |
| WO | 2021081174 A1 | 4/2021 |
| WO | 2023064325 A1 | 4/2023 |

OTHER PUBLICATIONS

Zuo, J. Y. et al., "A New Fluid Property—Insitu Formation Volume Factors from Formation Testing", SPWLA-2016-0000, presented at the 2016 SPWLA 57th Annual Logging Symposium, Reykjavik, Iceland, 15 pages.

(Continued)

*Primary Examiner* — Suman K Nath
(74) *Attorney, Agent, or Firm* — Jeffrey D. Frantz

(57) ABSTRACT

Systems and methods presented herein generally relate to a formation testing platform for quantifying and monitoring deep transient testing (DTT) surface gas rates using formation testing data collected by a downhole well tool, which may be adjusted based on surface gas rates directly measured by surface equipment. For example, a method includes flowing one or more fluids from a subterranean formation to flow through a downhole well tool disposed in a wellbore of a well during a deep transient testing (DTT) operation performed by the downhole well tool. The method also includes measuring data related to one or more properties of the one or more fluids using one or more downhole fluid analysis sensors disposed within the downhole well tool, and predicting, via a control system, a first predicted DTT surface gas rate based on the data measured related to the one or more properties of the one or more fluids.

20 Claims, 8 Drawing Sheets

90

92 — Determine how many different fluids are flowing (e.g., focused or unfocused flow)

94 — Map a flowrate to a fluid density estimation/ measurement to each different fluid 96 — Sum the flowrate for similar fluids 98 — Convert volume rate to mass rate by multiplying the summed volume rates to the mapped density

(51) Int. Cl.
　　E21B 21/08　　　(2006.01)
　　G01N 9/00　　　(2006.01)

(56) References Cited

U.S. PATENT DOCUMENTS

| | | | |
|---|---|---|---|
| 7,526,953 | B2 | 5/2009 | Goodwin |
| 7,920,970 | B2 | 4/2011 | Zuo |
| 7,966,273 | B2 | 6/2011 | Hegeman |
| 8,510,242 | B2 | 8/2013 | Al-Fattah |
| 8,805,617 | B2 | 8/2014 | Zuo |
| 9,128,203 | B2 | 9/2015 | Al-Dossary |
| 9,322,268 | B2 | 4/2016 | Zuo |
| 9,416,647 | B2 | 8/2016 | Zuo |
| 10,073,042 | B2 | 9/2018 | Wang |
| 10,316,656 | B2 | 6/2019 | Zuo |
| 10,585,082 | B2 | 3/2020 | Zuo |
| 10,781,686 | B2 | 9/2020 | Wang |
| 2009/0288881 | A1 | 11/2009 | Mullins |
| 2010/0169020 | A1 | 7/2010 | Niu |
| 2013/0103627 | A1 | 4/2013 | Maddinelli |
| 2014/0110167 | A1 | 4/2014 | Goebel |
| 2014/0238122 | A1 | 8/2014 | Mostowfi |
| 2014/0360259 | A1 | 12/2014 | Indo |
| 2015/0308264 | A1 | 10/2015 | Zuo |
| 2016/0091389 | A1 | 3/2016 | Zuo |
| 2016/0146004 | A1 | 5/2016 | Wang |
| 2017/0269252 | A1 | 9/2017 | Fang |
| 2020/0378814 | A1 | 12/2020 | Layher |
| 2021/0285927 | A1 | 9/2021 | Baecker |
| 2021/0324736 | A1 | 10/2021 | Edmundson |
| 2023/0349286 | A1* | 11/2023 | Jiang ..................... E21B 47/06 |
| 2023/0383649 | A1* | 11/2023 | Valero .................. E21B 49/088 |
| 2024/0401422 | A1* | 12/2024 | Kaipov ................ E21B 49/087 |
| 2025/0116589 | A1 | 4/2025 | Gisolf |

OTHER PUBLICATIONS

Search Report and Written Opinion of International Patent Application No. PCT/US2024/036869 dated Oct. 18, 2024, 10 pages.
Search Report and Written Opinion of International Patent Application No. PCT/US2023/016362 Dated Jul. 26, 2023, 11 pages.

Bagheripour et al., Support Vector Regression Between PVT Data and Bubble Point Pressure. Journal of Petroleum Exploration and Production Technology, Mar. 2, 2014. pp. 227-231.
El-Sebakhy et al., Support Vector Machines Framework for Predicting the PVT Properties of Crude Oil Systems. SPE Middle East Oil and Gas Show and Conference, Mar. 11-14, 2007. Bahrain. SPE-105698.
Fayazi et al., State-of-the-Art Least Square Support Vector Machine Application for Accurate Determination of Natural Gas Viscosity. Industrial Engineering Chemistry Research, 2014 vol. 53, pp. 945-958.
Hegeman et al., Application of Artificial Neural Networks to Downhole Fluid Analysis. Feb. 2009, SPE Reservoir Evaluation and Engineering, pp. 7-13. SPE 123423.
Majidi et al., Evolving an Accurate Model Based on Machine Learning Approach for Prediction of Dew-Point Pressure in Gas Condensate Reservoirs. Chemical Engineering Research and Design, 2014 vol. 92 (5), pp. 891-902.
Osman et al. Prediction of Oil PVT Properties Using Neural Networks. SPE Middle East Oil Show. Mar. 17-20, 2001. 14 pages, Society of Petroleum Engineers, SPE-68233.
Siddigui, F., "A Derivative-less Approach for Generating Phase Envelopes", Oil Gas Research, 2015, 1: 106, 6 pages.
Whitson, C. H. Characterizing Hydrocarbon Plus Fractions. Society of Petroleum Engineers Journal, 1983, 23(04), 683-694. SPE-12233.
Zuo et al., EOS-Based Downhole Fluid Characterization. Society of Petroleum Engineers Journal vol. 16 (1), Mar. 2011, pp. 115-124.
Zuo et al., Plus fraction characterization and PVT data regression for reservoir fluids near critical conditions. SPE Asia Pacific Oil and Gas Conference and Exhibition. Oct. 16-18, 2000, 12 pages, Society of Petroleum Engineers, Brisbane, Australia, SPE-64520.
Notice of Allowance issued in U.S. Appl. No. 15/193,519 dated May 15, 2020, 9 pages.
Office Action issued in U.S. Appl. No. 15/193,519 dated Feb. 6, 2020, 7 pages.
Office Action issued in U.S. Appl. No. 15/193,519 dated Aug. 13, 2019, 10 pages.
Office Action issued in U.S. Appl. No. 15/193,519 dated Jan. 8, 2019, 15 pages.
Office Action issued in U.S. Appl. No. 15/193,519 dated Jun. 22, 2018, 29 pages.

* cited by examiner

90

92 Determine how many different fluids are flowing (e.g., focused or unfocused flow)

94 Map a flowrate to a fluid density estimation/ measurement to each different fluid 96 Sum the flowrate for similar fluids 98 Convert volume rate to mass rate by multiplying the summed volume rates to the mapped density

112

114 — Determine the total number of moles of gas released at the surface for each component by dividing the mass by molecular weight 116 — Determine the total volume of gas released at the surface for each component by multiplying the number of moles by their molecular volume 118 — Optional: Sum the volumes to determine total gas volume

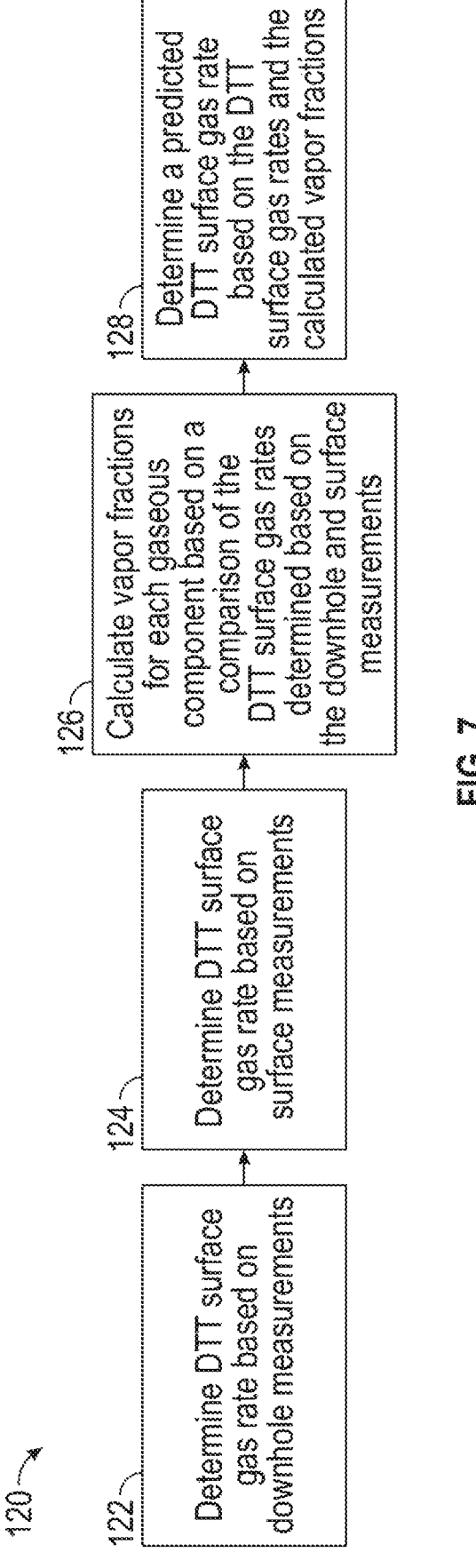

120

122 — Determine DTT surface gas rate based on downhole measurements

124 — Determine DTT surface gas rate based on surface measurements

126 — Calculate vapor fractions for each gaseous component based on a comparison of the DTT surface gas rates determined based on the downhole and surface measurements 128 — Determine a predicted DTT surface gas rate based on the DTT surface gas rates and the calculated vapor fractions

FIG. 7

DEEP TRANSIENT TESTING (DTT) DOWNHOLE AND SURFACE GAS RATE INTEGRATION WORKFLOW

This application claims the benefit of U.S. Provisional Application No. 63/512,107, entitled "DEEP TRANSIENT TESTING (DTT) DOWNHOLE AND SURFACE GAS RATE INTEGRATION WORKFLOW" filed Jul. 6, 2023, the disclosure of which is hereby incorporated herein by reference.

BACKGROUND

The present disclosure generally relates to a formation testing platform for quantifying and monitoring hydrocarbon volumes and surface gas emissions using formation testing data collected by the formation testing platform and integrated with data directly measured at the surface.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as an admission of any kind.

Hydrocarbons and associated gas or free gas that is pumped into the wellbore during sampling and pressure transient testing operations will eventually reach the surface. During deep transient testing (DTT) operations, hydrocarbons are circulated to surface together with circulated mud. Once on surface, hydrocarbon (and non-hydrocarbon) gases may be separated, and the gas may either be vented to the atmosphere or burned (e.g., flared).

SUMMARY

A summary of certain embodiments described herein is set forth below. It should be understood that these aspects are presented merely to provide the reader with a brief summary of these certain embodiments and that these aspects are not intended to limit the scope of this disclosure.

Certain embodiments of the present disclosure include a method that includes allowing one or more fluids from a subterranean formation to flow through a downhole well tool disposed in a wellbore of a well during a deep transient testing (DTT) operation performed by the downhole well tool. The method also includes predicting, via a control system, a predicted DTT surface gas rate based at least in part on measurement data relating to one or more properties of the one or more fluids.

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings, in which:

FIG. 7 is a flow diagram of a workflow that may be utilized to fine tune determined DTT surface gas rates based on both downhole measurements and surface measurements, in accordance with embodiments of the present disclosure.

DETAILED DESCRIPTION

Figure 1:
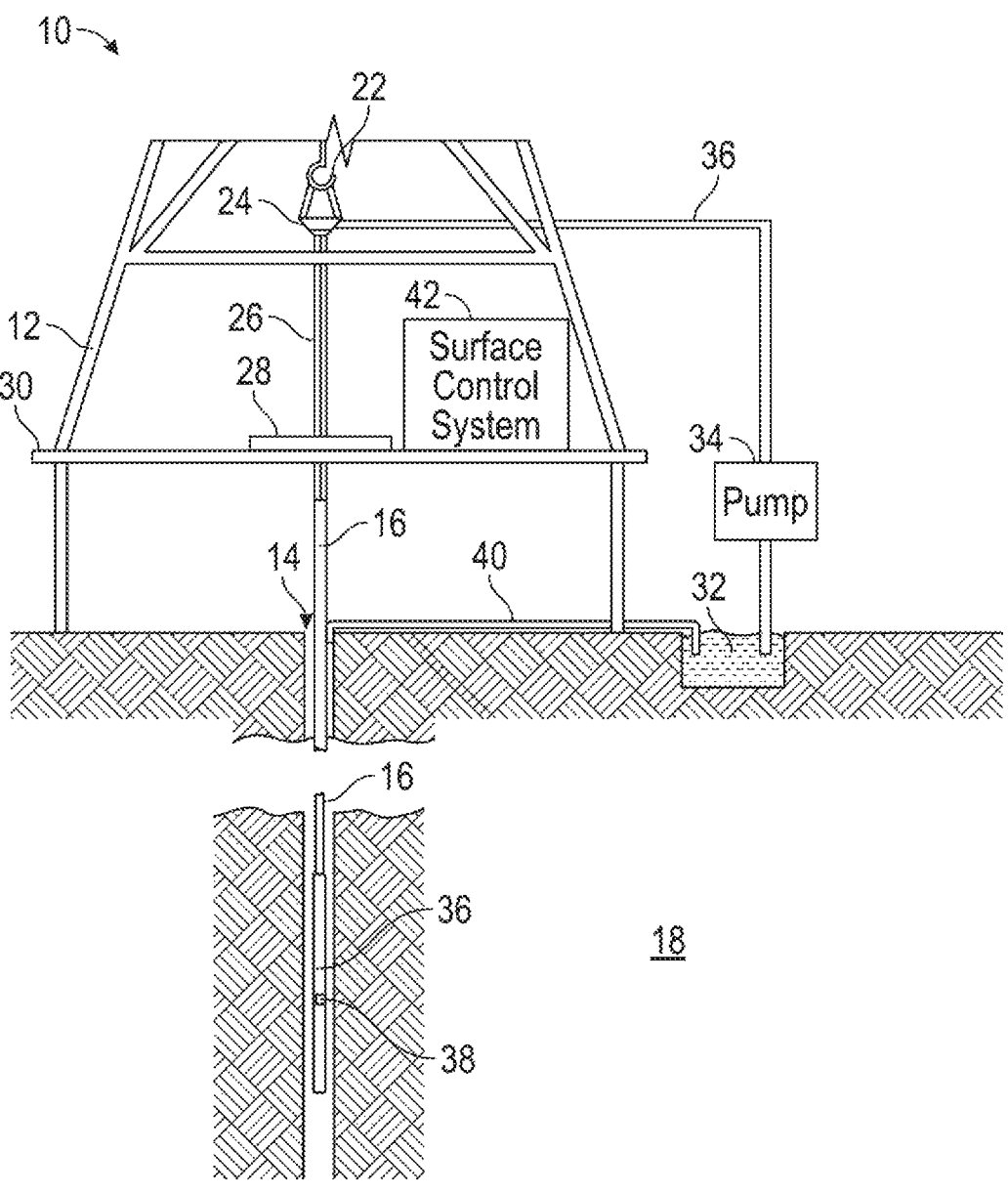
FIG. 1 is a schematic illustration of a well system, in accordance with embodiments of the present disclosure.

One or more specific embodiments of the present disclosure will be described below. These described embodiments are only examples of the presently disclosed techniques. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

As used herein, the terms "connect," "connection," "connected," "in connection with," and "connecting" are used to mean "in direct connection with" or "in connection with via one or more elements"; and the term "set" is used to mean "one element" or "more than one element." Further, the terms "couple," "coupling," "coupled," "coupled together," and "coupled with" are used to mean "directly coupled together" or "coupled together via one or more elements." As used herein, the terms "up" and "down," "uphole" and "downhole", "upper" and "lower," "top" and "bottom," and other like terms indicating relative positions to a given point or element are utilized to more clearly describe some elements. Commonly, these terms relate to a reference point as the surface from which downhole operations are initiated as being the top (e.g., uphole or upper) point and the total depth being the lowest (e.g., downhole or lower) point, whether the well (e.g., wellbore, borehole) is vertical, horizontal or slanted relative to the surface.

In addition, as used herein, the terms "real time", "real-time", or "substantially real time" may be used interchangeably and are intended to describe operations (e.g., computing operations) that are performed without any human-perceivable interruption between operations. For example, as used herein, data relating to the systems described herein may be collected, transmitted, and/or used in control computations in "substantially real time" such that data readings, data transfers, and/or data processing steps occur once every second, once every 0.1 second, once every 0.01 second, or even more frequently, during operations of the systems (e.g., while the systems are operating). In addition, as used herein, the terms "continuous", "continuously", or "continually" are intended to describe operations that are performed without any significant interruption. For example, as used herein, control commands may be transmitted to certain equipment every five minutes, every minute, every 30 seconds, every 15 seconds, every 10 seconds, every 5 seconds, or even more often, such that operating parameters of the equipment may be adjusted without any significant interruption to the closed-loop control of the equipment. In addition, as used herein, the terms "automatic", "automated", "autonomous", and so forth, are intended to describe operations that are performed are caused to be performed, for example, by a computing system (i.e., solely by the computing system, without human intervention).

The formation testing platform described herein provides measurements of pressure, temperature, volumetric flow-rate, and total flowed volume, among other operational parameters, versus elapsed time. In addition, the embodiments described herein include downhole fluid analysis (DFA) sensors to measure and determine fluid properties such as hydrocarbon composition (e.g., weight fractions of $CO_2$, $C_1$, $C_2$, $C_3$, $C_4$, $C_5$, $C_6$+, and so forth), fluid density, mud filtrate contamination level, gas/oil ratio (GOR), and formation volume factors, among other properties, during a test station. Through integration of the DFA sensor measurements with the station transient data such as flowrate, mass and molar flowrates may be derived for each component, and the total mass and mole of gas pumped from the formation may be derived, in substantially real time every time fluid is pumped out from the formation into the wellbore. The mass rate of the individual components can then be converted to surface rates and surface volumes, thereby enabling accurate determination of surface gas rate resulting from any downhole fluid pumped during formation testing and sampling operations.

In addition, the embodiments described herein include a workflow to enable effective monitoring and control of surface gas emissions during formation testing operations. The ability to quantify and monitor surface emissions is also an important first step to help enable reductions in $CO_2$ and greenhouse gas emissions, which also aligns with global sustainable development goals. Furthermore, the embodiments described herein include a workflow to integrate surface gas measurements with the predicted rate from downhole measurements during formation testing operations.

Turning now to the drawings, a well system 10 is illustrated in FIG. 1. As illustrated, the well system 10 includes a drilling rig 12 positioned over a wellbore 14. Although illustrated as an onshore well system 10, it is noted that the drilling system could instead be an offshore drilling system. In certain embodiments, the drilling rig 12 supports a drill string 16 that extends downhole into the wellbore 14 through a geological formation 18.

In certain embodiments, the drill string 16 may be suspended within the wellbore 14 from a hook 22 of the drilling rig 12 via a swivel 24 and a kelly 26. Although not illustrated in FIG. 1, it will be appreciated that the hook 22 may be connected to a hoisting system used to raise and lower the drill string 16 within the wellbore 14. As but one non-limiting example, such a hoisting system may include a crown block and a drawworks that cooperate to raise and lower a traveling block (to which the hook 22 is connected) via a hoisting line. The kelly 26 is coupled to the drill string 16, and the swivel 24 allows the kelly 26 and the drill string 16 to rotate with respect to the hook 22. In certain embodiments, a rotary table 28 on a drill floor 30 of the drilling rig 12 may be configured to grip and turn the kelly 26 to drive rotation of the drill string 16 to drill the wellbore 14. In other embodiments, however, a top drive system may instead be used to drive rotation of the drill string 16.

During operation, drill cuttings or other debris may collect near the bottom of the wellbore 14. Drilling fluid 32, also referred to as drilling mud, may be circulated through the wellbore 14 to remove this debris. The drilling fluid 32 may also clean and cool a drill bit disposed at a bottom of the drill string 16 and provide positive pressure within the wellbore 14 to inhibit formation fluids from entering the wellbore. In the embodiment illustrated in FIG. 1, the drilling fluid 32 is circulated through the wellbore 14 by a pump 34. In addition, the drilling fluid 32 is pumped from a mud pit (or some other reservoir, such as a mud tank) into the drill string 16. In general, the drilling fluid 32 exits near the bottom of the drill string 16 and returns to the surface of the well system 10 between the wellbore 14 and the drill string 16. A return conduit 40 may transfer the returning drilling fluid 32 away from the wellbore 14. In certain embodiments, the returning drilling fluid 32 may be cleansed (e.g., via one or more shale shakers, desanders, or desilters) and reused in the wellbore 14.

As described in greater detail herein, the well system 10 may also include a surface control system 42 located at a surface location of the well system 10, which is configured to control operation of the various equipment of the well system 10, including a downhole well tool 36 conveyed into the wellbore 14 via the drill string 16. In addition, in certain embodiments, the downhole well tool 36 may include a tool control system 38 that controls the local functionality of the downhole well tool 36. In certain embodiments, the tool control system 38 of the downhole well tool 36 may communicate with the surface control system 42 such that the control systems 38, 42 collectively control operation of the downhole well tool 36. As will be appreciated, the tool control system 38 of the downhole well tool 36 may include components that are substantially similar to the components of the surface control system 42.

Figure 2:
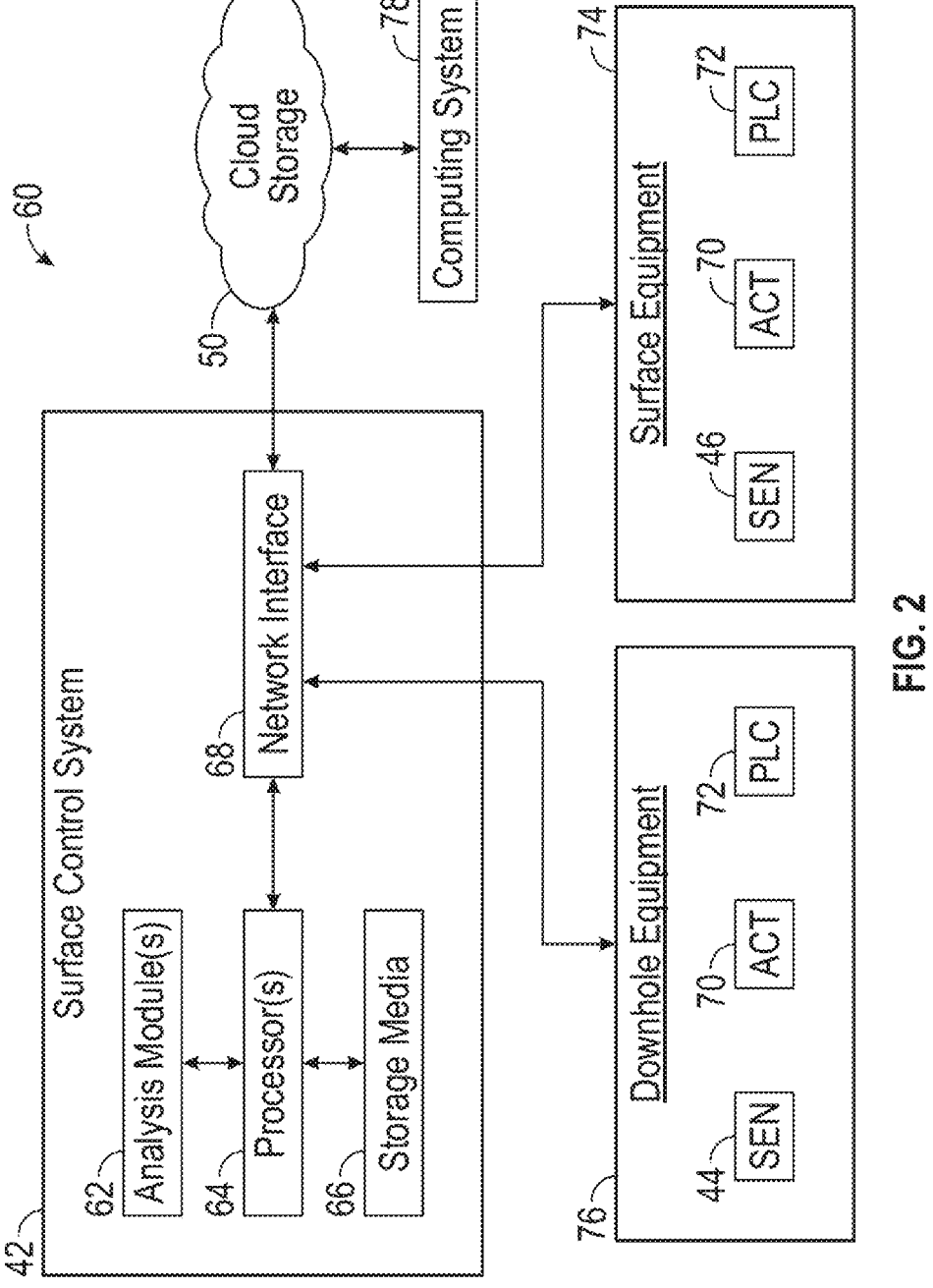
FIG. 2 illustrates a well control system that may include a surface control system to control the well system described herein, in accordance with embodiments of the present disclosure.

FIG. 2 illustrates a well control system 60 that may include the surface control system 42 to control the well system 10 described herein. In certain embodiments, the surface control system 42 may include one or more analysis modules 62 (e.g., a program of computer-executable instructions and associated data) that may be configured to perform various functions of the embodiments described herein. In certain embodiments, to perform these various functions, an analysis module 62 executes on one or more processors 64 of the surface control system 42, which may be connected to one or more storage media 66 of the surface control system 42. Indeed, in certain embodiments, the one or more analysis modules 62 may be stored in the one or more storage media 66.

In certain embodiments, the one or more processors 64 may include a microprocessor, a microcontroller, a processor module or subsystem, a programmable integrated circuit, a programmable gate array, a digital signal processor (DSP), or another control or computing device. In certain embodiments, the one or more storage media 66 may be implemented as one or more non-transitory computer-readable or machine-readable storage media. In certain embodiments, the one or more storage media 66 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the computer-executable instructions and associated data of the analysis module(s) 62 may be provided on one computer-readable or machine-readable storage medium of the storage media 66, or alternatively, may be provided on multiple computer-readable or machine-readable storage media distributed in a large system having possibly plural nodes. Such computer-readable or machine-readable storage medium or media are considered to be part of an article (or article of manufacture), which may refer to any manufactured single component or multiple components. In certain embodiments, the one or more storage media 66 may be located either in the machine running the machine-readable instructions, or may be located at a remote site from which machine-readable instructions may be downloaded over a network for execution.

In certain embodiments, the processor(s) 64 may be connected to a network interface 68 of the surface control system 42 to allow the surface control system 42 to communicate with various downhole sensors 44 and surface sensors 46 described herein, as well as communicate with actuators 70 and/or PLCs 72 of surface equipment 74 (e.g., the pump 34, and so forth, illustrated in FIG. 1) and of downhole equipment 76 (e.g., the downhole well tool 36, and so forth, illustrated in FIG. 1) for the purpose of controlling operation of the well system 10, as described in greater detail herein. In certain embodiments, the network interface 68 may also facilitate the surface control system 42 to communicate data to cloud storage 50 (or other wired and/or wireless communication network) to, for example, archive the data or to enable external computing systems 78 to access the data and/or to remotely interact with the surface control system 42.

It should be appreciated that the well control system 60 illustrated in FIG. 2 is only one example of a well control system, and that the well control system 60 may have more or fewer components than shown, may combine additional components not depicted in the embodiment of FIG. 2, and/or the well control system 60 may have a different configuration or arrangement of the components depicted in FIG. 2. In addition, the various components illustrated in FIG. 2 may be implemented in hardware, software, or a combination of both hardware and software, including one or more signal processing and/or application specific integrated circuits. Furthermore, the operations of the well control system 60 as described herein may be implemented by running one or more functional modules in an information processing apparatus such as application specific chips, such as application-specific integrated circuits (ASICs), field-programmable gate arrays (FPGAs), programmable logic devices (PLDs), systems on a chip (SOCs), or other appropriate devices. These modules, combinations of these modules, and/or their combination with hardware are all included within the scope of the embodiments described herein.

As described above, the embodiments described herein include a downhole well tool 36 configured to perform reservoir fluid analysis by drawing in formation fluid and testing the formation fluid downhole or collecting a sample of the formation fluid to bring to the surface. For example, in certain embodiments, the downhole well tool 36 may use a probe and/or packers to isolate a desired region of the wellbore 14 (e.g., at a desired depth) and establish fluid communication with the subterranean formation 18 surrounding the wellbore 14. The probe may draw the formation fluid into the downhole well tool 36. In certain embodiments, the downhole well tool 36 may include a hydraulic module configured to control the flow of fluid through fluid lines of the downhole well tool 36, and a probe that includes one or more inlets for receiving the fluid through the fluid lines of the downhole well tool 36. In certain embodiments, the probe may include multiple inlets (e.g., a sampling probe and a guard probe) that may be used for the sampling described herein. In certain embodiments, the probe may be movable between extended and retracted positions for selectively engaging the wellbore 14 and acquiring fluid samples from the formation 18. As described in greater detail herein, the downhole well tool 36 may also include a fluid analysis module configured to analyze the fluid flowing through the flowlines. In addition, the downhole well tool 36 may include one or more fluid collecting chambers configured to store the fluid samples.

Figure 3:
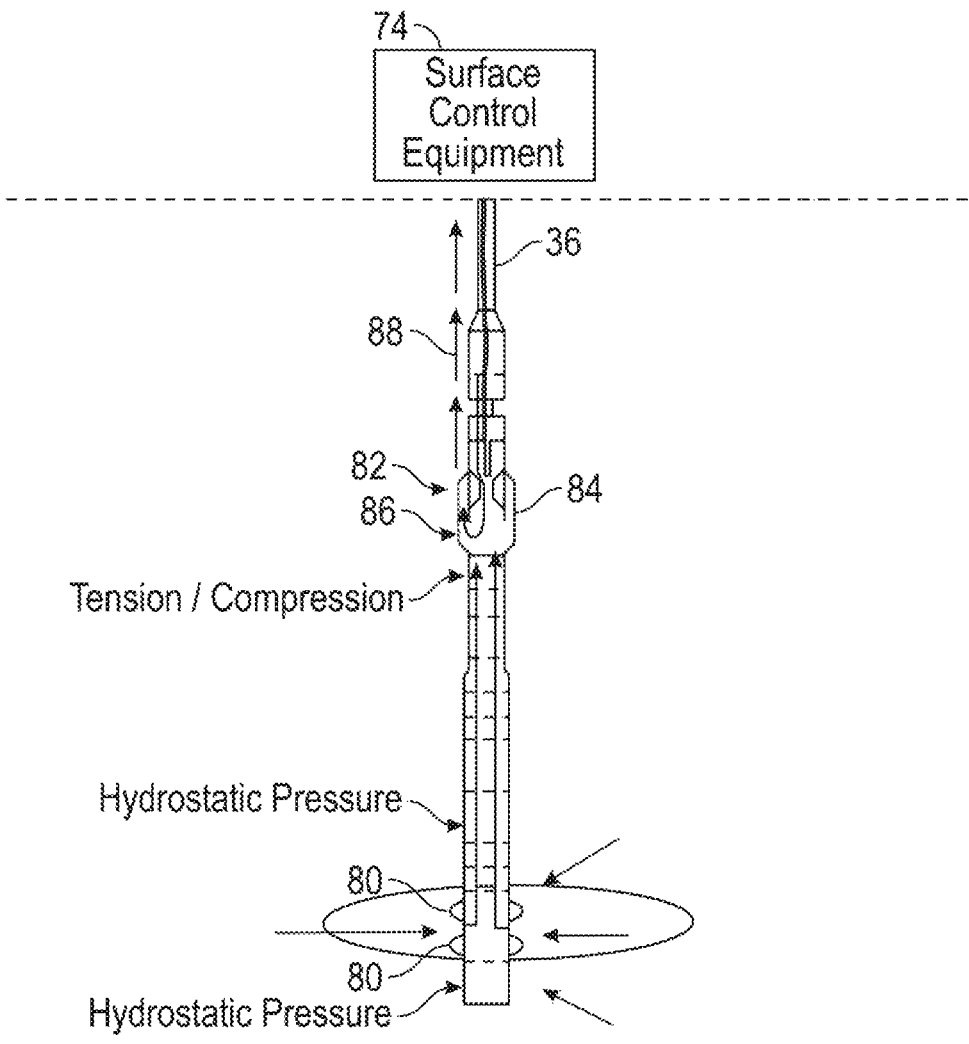
FIG. 3 is a side view of a downhole well tool, in accordance with embodiments of the present disclosure.

As described in greater detail herein, the embodiments described herein provide systems and methods for producing hydrocarbons during transient testing of a well (e.g., as performed by the downhole well tool 36 illustrated in FIG. 1), and cleaning the well. FIG. 3 illustrates a downhole well tool 36 that may be lowered to a target depth within a wellbore 14 (e.g., conveyed by drill pipe or other conveyance mechanism) to test a hydrocarbon-bearing formation 18 through which the wellbore 14 extends. Once the downhole well tool 36 is lowered to the target depth, a production test may be conducted by the downhole well tool 36, after inflating dual packers 80 at the bottom of the downhole well tool 36 and flowing the native fluid in the downhole well tool 36, and the produced fluid is conveyed up the toolstring to the tubing circulation head 82 (or, right below, at the level of a flow exit port 84) where the wellbore mud is mixed with the hydrocarbons (e.g., in a mud mixing chamber 86 of the tubing circulation head 82). Throughout the operation, well control may be maintained via the surface equipment 74 (e.g., the pump 34 illustrated in FIG. 1), and the hydrocarbon/wellbore mud mix may be circulated out (arrow 88) to flowback equipment of the well system 10.

As discussed above, the embodiments described herein include a workflow to enable effective monitoring and control of surface gas emissions during formation testing operations. The ability to quantify and monitor surface emissions is also an important first step to help enable reductions in $CO_2$ and greenhouse gas emissions, which also aligns with global sustainable development goals. Furthermore, the embodiments described herein include a workflow to integrate surface gas measurements with the predicted rate from downhole measurements during formation testing operations.

1) Determining DTT Surface Gas Rate Based on Downhole Measurements

Figure 4:
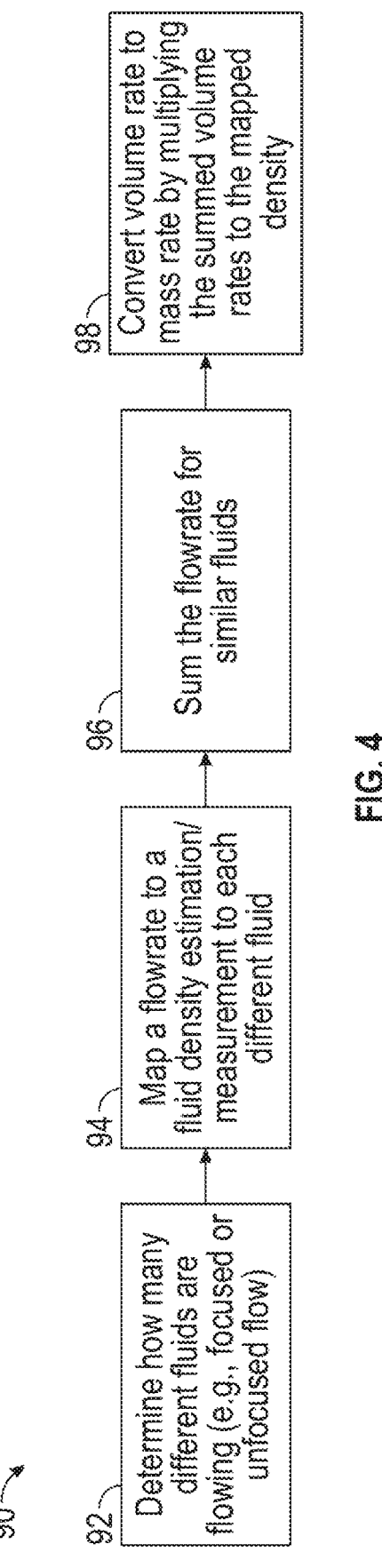
FIG. 4 is a flow diagram of a workflow that may be utilized by the downhole well tool to determine the total mass rate of the fluid flowing through the downhole well tool, in accordance with embodiments of the present disclosure.

FIG. 4 is a flow diagram of a workflow 90 that may be utilized to determine the total mass rate of the fluid flowing through the downhole well tool 36. As illustrated, in certain embodiments, the workflow 90 may include determining how many different fluids (e.g., 1, 2, or even more) are flowing (e.g., either focused or unfocused flow) through the downhole well tool 36 (block 92). In addition, in certain embodiments, the workflow 90 may include mapping a flowrate to a fluid density estimation and/or measurement for each different fluid (block 94). In addition, in certain embodiments, the workflow 90 may include summing the flowrates for similar fluids (block 96). In addition, in certain embodiments, the workflow 90 may include converting volume rate to mass rate by multiplying the summed volume rates to the mapped density (block 98). It should be noted that fluid density may either be directly measured with a fluid density sensor of the downhole well tool 36 or estimated using fluid compositional measurements and a fluid model.

The gas mass for each component in a pumped mixture (of hydrocarbon and filtrate) is of particular importance in dynamic well control (e.g., predicting the interaction of pumped fluids with the mud in the wellbore 14) and to track the mass of pumped gas and surface gas emissions. By computing this quantitative indicator in substantially real time, a pumped gas log may be generated for real-time monitoring and control.

For wells containing oil-based mud (OBM), the hydrocarbon will dissolve in the wellbore mud. When circulated to the surface, most of the gaseous components will come out of solution and may be vented to the atmosphere as free gas (or potentially flared or otherwise treated). The fraction of gas that comes out of solution at the surface is called the vapor fraction. The vapor fractions of $CO_2$, $C_1$, $C_2$, $C_3$, $C_4$ and $C_5$ depends on the type of oil, while $C_6+$ is mainly a liquid component. The vapor fractions may be estimated in many different ways, including empirical methods, correlations, or by using a convolutional neural network (CNN) model, a recurrent neural network (RNN) model, or an artificial neural network (ANN) model, or other model. In certain embodiments, the input to determine the vapor fractions may be based on the measured fluid GOR, density, other measured fluid properties, and potentially mud-type and circulation rate. Alternatively, some vapor fractions may be set to 1 for certain mud/hydrocarbon combinations. For example, in the case of wells containing water-based mud (WBM) the $CO_2$, $C_1$, and $C_2$ vapor fractions might be set to 1. Note that in certain environments, it may be preferred to estimate an upper limit of the pumped gas rather than taking the risk of underestimation. Therefore, under certain scenarios, the vapor fractions of $C_3$-$C_5$ may be regarded as 1 if there is no better estimation.

Figure 5:
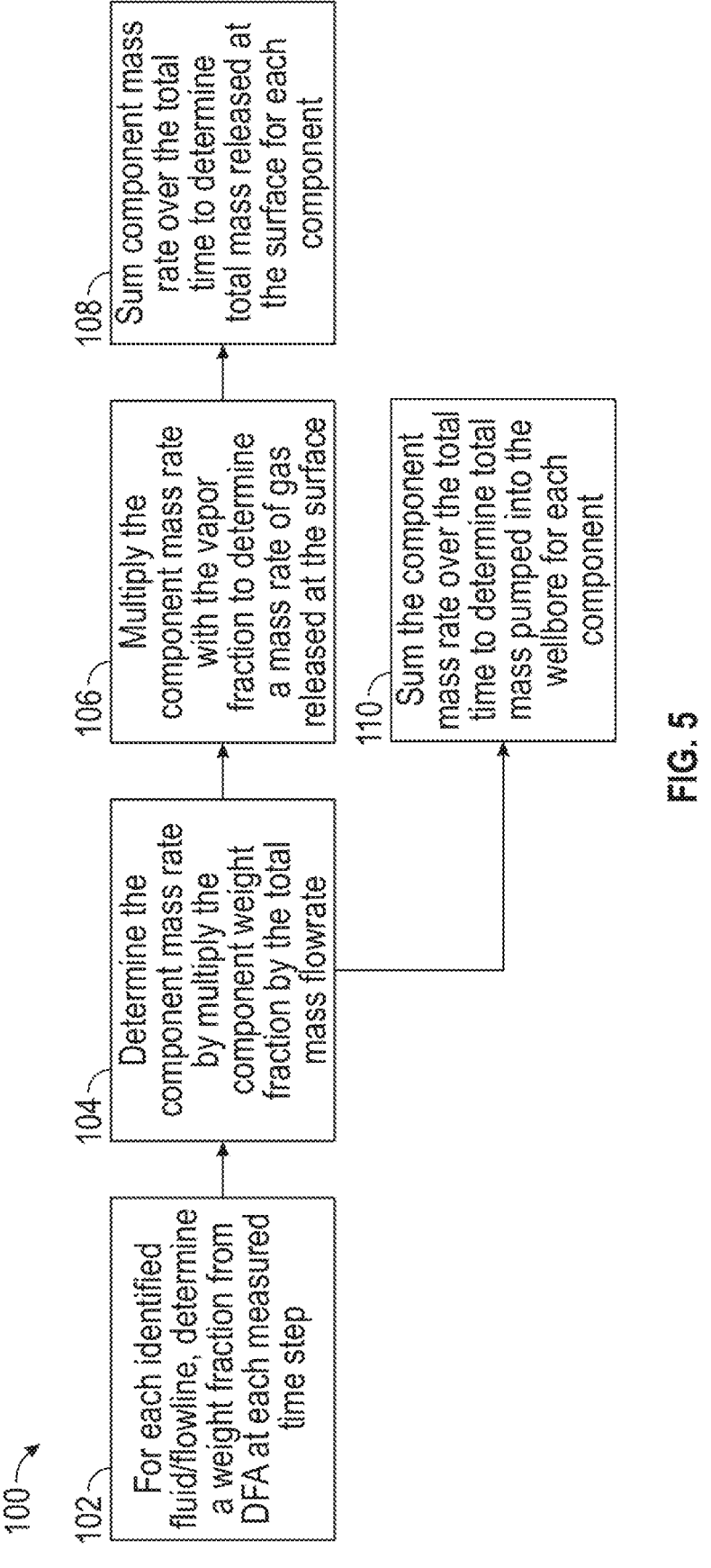
FIG. 5 is a flow diagram of a workflow that may be utilized by the downhole well tool to determine the total mass rate of gas, in accordance with embodiments of the present disclosure.

FIG. 5 is a flow diagram of a workflow 100 that may be utilized to determine the total mass rate of gas. As illustrated, in certain embodiments, the workflow 100 may include, for each fluid/flowline identified in the workflow 90 illustrated in FIG. 4, determining a weight fraction from DFA at each measured time step (block 102). In addition, in certain embodiments, the workflow 100 may include determining the mass rate of each component of the fluid by multiplying the weight fraction of each component by the total mass flowrate (block 104). In addition, in certain embodiments, the workflow 100 may include multiplying the component mass rate calculated in block 104 with the vapor fraction, which may be determined as described above, to determine a mass rate of gas released at the surface (block 106). In addition, in certain embodiments, the workflow 100 may include summing the component mass rate over the total time to determine total mass of gas released at the surface for each component (block 108). In addition, in certain embodiments, the workflow 100 may also include summing the component mass rate calculated in block 104 over the total time to determine total mass pumped into the wellbore 14 for each component (block 110).

Figure 6:
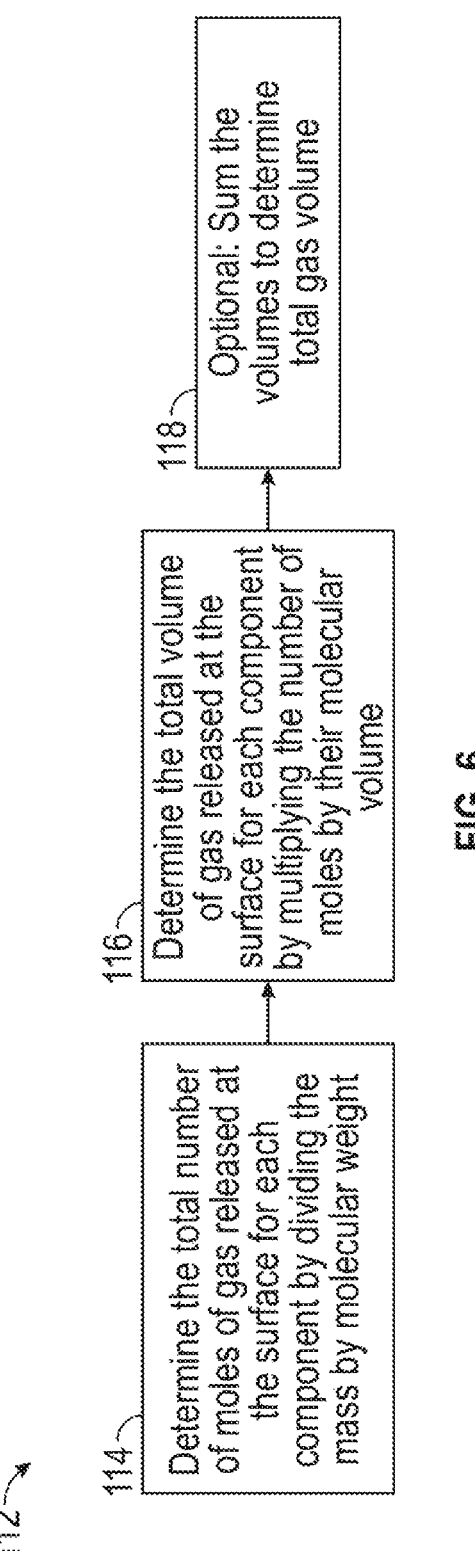
FIG. 6 is a flow diagram of a workflow that may be utilized by the downhole well tool to determine the total pumped gas volume accumulated at the surface at standard conditions for each component from the various fluids/flowlines, in accordance with embodiments of the present disclosure.

FIG. 6 is a flow diagram of a workflow 112 that may be utilized to determine the total pumped gas volume accumulated at the surface at standard conditions for each component from the various fluids/flowlines. As illustrated, in certain embodiments, the workflow 112 may include determining the total number of moles of gas released at the surface for each component by dividing the mass by molecular weight (block 114). In addition, in certain embodiments, the workflow 112 may include determining the total volume of gas released at the surface for each component by multiplying the number of moles by their respective molecular volume (block 116). In addition, in certain embodiments, the workflow 112 may optionally include summing the volumes to determine total gas volume (block 118). In certain embodiments, each of the steps of the workflow 112 may be performed by the surface control system 42. Table 1 illustrates molar weights of each gas component ($MW_j$).

TABLE 1

| Molar weights of each gas component. | |
| --- | --- |
| Component | Molar Weight (g/mole) |
| Methane | 16.04 |
| Ethane | 30.07 |
| Propane | 44.10 |
| Butane | 58.12 |
| Pentane | 72.15 |
| $CO_2$ | 44.01 |

Alternatively, in certain embodiments, the individual component mass rates determined in the workflow 100 may be determined by dividing the mass of each component by total molecular weight first to determine the molecular rate, which may then be multiplied by the total molecular volume to determine the individual volume rates of each component. These can be summed over time to determine the individual component total volume at the surface.

In certain embodiments, determining the actual gas emission rates at the surface at standard conditions during DTT operations includes combining the wellbore volume and mud circulation rates. The mass rate and volume rates predicted in workflows 100, 112 may arrive at the surface, delayed by the circulation time, which is the wellbore volume divided by the mud circulation rates.

In certain embodiments, both methane and carbon dioxide are considered "greenhouse gas". The mass and volume of these gases may be measured directly using the techniques described herein. Methane is much more potent than carbon dioxide when it comes to trapping heat in the atmosphere. It is, therefore, relatively important to be able to quantify the $CO_2$ equivalent effect of $CH_4$ and the $CO_2$ emissions in case $CH_4$ is flared. However, it is important to note measurements of $CH_4$ and $CO_2$ emissions are needed to be able to apply these conversions. The total gas may be assumed to be a summation of the gaseous components.

The information determined by the workflows 90, 100, 112 illustrated in FIGS. 4-6 may be used in various specific applications. As one non-limiting example, in certain embodiments, the hydrocarbon footprint of any formation testing operation may be quantified. An important step to do so includes quantifying the individual gas component volumes and the total $CO_2$ equivalent volume released to the atmosphere due to pumping fluids from the formation 18 with the downhole well tool 36.

As another example, in certain embodiments, the reduction of emissions compared to other technologies may be quantified. The ability to quantify the emissions of each method/technology is a relatively important first step in reducing the total emissions. During DTT operations, the volume pumped to generate the pressure-transient build up is considerably larger than during wireline formation testing operations, but orders of magnitude smaller than during drill string testing (DST) operations. However, during a DST operation, the produced emissions are typically flared. The reduced volumes during a DTT operation, compared to a DST operation, result in less produced hydrocarbons at the surface. However, without quantifying the actual volume of gas released at the surface, it may be relatively difficult to do a quantitative emission comparison between different services, to quantify the emission effects of DTT operation design changes, such as changing the flowrate, flow duration, or the number of stations, and to quantify the emission effects of changing mud type and circulation rates.

As another example, in certain embodiments, before a formation testing operation, the pressure and formation fluid volume pumping limits may be simulated in advance. Doing so may serve as the limiting factor in the amount of hydrocarbons allowed to pump into the well. During the formation testing operations, the downhole well tool 36 may pump fluids continuously, and the volume of pumped hydrocarbons or gas may either fully or partially dissolve in OBM or be suspended in the wellbore 14 in WBM environments. In both cases a plume of gas-cut mud may tend to initiate and then accumulate downhole in the wellbore 14 near the test interval depths. These hydrocarbon plumes tend to remain downhole until they are circulated out. In certain embodiments, the flowrate, composition, density, water fraction, and so forth, may be determined in substantially real time, and the methods described herein may be used to accurately estimate the total mass of gas. Formation testing operations may continue until the total gas mass limit is reached. The current limits are typically set based on total volume pumped rather than the mass of the gaseous components. It should be noted that because the amount of gas may be accurately estimated rather than relying on overly conservative limits (which is the current practice), the methods described herein allow unnecessary wiper trips to be prevented and mitigate potential well control risks.

2) Determining DTT Surface Gas Rate based on Surface Measurements

In addition to determining surface gas rate based on downhole measurements, the surface gas rate may be determined based on surface measurements. During operations, gas and mud are circulated to the surface in a mixed state. In OBM environments, the gas will be dissolved in the mud. Conversely, for WBM environments, relatively small bubbles will be suspended in the mud. For both scenarios, gas and mud will need to be separated to be able to measure the surface gas rate. In certain embodiments, a mud-gas separator (MGS) may be used to separate the gas from the mud. In such embodiments, the gas rate may be measured at the output side of the MGS with, for example, a relatively small orifice gas meter or a Coriolis or ultrasonic gas meter. Alternatively, in certain embodiments, a DST separator with some back pressure (e.g. 30 or 50 psi) may be placed before the MGS. The gas rate after the DST separator may be measured with, for example, using a multiphase flow meter. In certain embodiments, the mud from the DST separator may still be routed to the MGS, where the separated gas may also be measured (e.g., as described above). In such embodiments, the MGS may essentially be a second stage separator having its own gas rate measurement capability. In addition, in certain embodiments, for OBM environments, the mud may be routed to a vacuum degasser, and the gas extracted by the vacuum degasser may also be measured. It will be appreciated that any combination of these gas measurement techniques may be combined together to measure the gas composition sequentially. Specifically, a total compositional gas rate may be determined by summing the compositional gas rates at each stage.

3) Combining Downhole and Surface Gas Rate Measurements for OBM Systems

For OBM systems, most of the gaseous components will come out of solution at the surface. The fraction of gas that comes out of solution at the surface is called the vapor fraction. The vapor fractions of $CO_2$, $C_1$, $C_2$, $C_3$, $C_4$, and $C_5$ generally depends on the type of oil and mud. Any component above $C_5$ (e.g., $C_6$+) is expected to be predominantly in liquid phase at the surface, and is expected to remain dissolved in the mud.

As described above, in step 1, the surface gas rate and gas composition may be predicted based on downhole measurements, with an assumed vapor fraction of 1 for each gaseous component. Conversely, in step 2, the actual gas rate and gas composition may be directly measured, but with unknown vapor fraction. In general, the surface gas rate for each gaseous component that is measured at the surface should be smaller than the surface gas rate that is predicted based on the downhole measurements, with the difference assumed to be caused by the component vapor fraction.

FIG. 7 is a flow diagram of a workflow 120 that may be utilized to fine tune the DTT surface gas rates determined in steps 1 and 2. As illustrated, in certain embodiments, the workflow 120 may include determining DTT surface gas rate based on downhole measurements (e.g., according to step 1, as illustrated in FIGS. 4-6 and described in the associated paragraphs above) (block 122). In addition, in certain embodiments, the workflow 120 may include determining DTT surface gas rate based on surface measurements (e.g., according to step 2, as described above) (block 124). In addition, in certain embodiments, the workflow 120 may include calculating vapor fractions for each gaseous component based on a comparison of the DTT surface gas rates determined based on the downhole and surface measurements, respectively (e.g., of steps 1 and 2, respectively)

(block 126). Then, in certain embodiments, the workflow 120 may include determining predicted DTT surface gas rate based on the DTT surface gas rates determined based on the downhole measurements, the DTT surface gas rates determined based on the surface measurements, and the calculated vapor fractions (block 128).

As such, by comparing the surface gas rate determined using step 1 (i.e., surface gas rate from DFA) to the surface gas rate determined using step 2 (i.e., surface gas rate measured at the surface) for each gaseous component, the vapor fraction may be estimated (calculated). For longer jobs where mud is re-circulated, the amount of gaseous components that may be added to the active mud system may reduce over time, making this value relatively difficult to predict. However, the workflows described herein may be used to quantify the volume (or mass) of gaseous components added to the mud system, which is valuable for predicting if the mud may be re-circulated back into the well or if the mud system requires treatment before being used on subsequent wells, or before disposal. In addition, if the volume of gaseous components added to the mud system is ignored, the surface gas rate measurements may underestimate the true gas rate.

It should be noted that, with flare gas-in versus gas-out measurements, differences in the type and quantity of gas that is dissolved in the mud can be measured. In general, this mud composition measurement should correlate with the quantity of dissolved gas in the mud system as measured from DFA (combined with circulation rates). By measuring the quantity of gas added to the mud system, the flare measurements may be calibrated, which are relatively accurate in the ration of gaseous components, but not as good in estimating the absolute quantities of gaseous components.

4) Combining Downhole and Surface Gas Rate Measurements for WBM Systems

In WBM systems, separating gaseous components from the WBM is relatively much more efficient. The above described workflows still apply, but there will be much less gas remaining in the mud system. However, the workflows described herein may also be important for gas rate measurement quality control. In general, the surface gas rate predicted from downhole measurements should equal the surface gas rate measurements. However, discrepancies may indicate separator efficiency problems, or possibly gas vented outside the measure points (e.g. the mud trough), or indicate measurement accuracy issues.

It will be appreciated that the surface control system 42 described above may perform much of the processing and control functions described herein. However, as described above, the downhole well tool 36 includes a tool control system 38 that controls the local functionality of the downhole well tool 36. In certain embodiments, the tool control system 38 of the downhole well tool 36 may communicate with the surface control system 42 such that the control systems 38, 42 collectively control operation of the downhole well tool 36 (and may be collectively referred to as a "control system"). As will be appreciated, the tool control system 38 of the downhole well tool 36 may include components that are substantially similar to the components of the surface control system 42 illustrated in FIG. 2.

Figure 8:
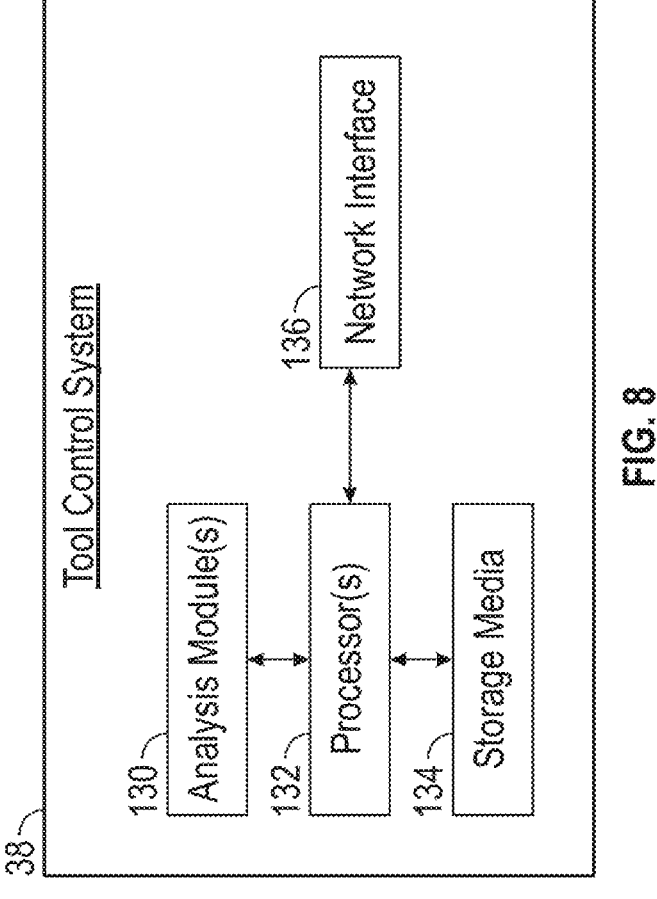
FIG. 8 illustrates an embodiment of the tool control system illustrated in FIG. 1, in accordance with embodiments of the present disclosure.

FIG. 8 illustrates an embodiment of the tool control system 38 illustrated in FIG. 1. In certain embodiments, the tool control system 38 may include one or more analysis modules 130 (e.g., a program of processor executable instructions and associated data) that may be configured to perform various functions of the embodiments described herein. In certain embodiments, to perform these various functions, an analysis module 130 executes on one or more processors 132 of the tool control system 38, which may be connected to one or more storage media 134 of the tool control system 38. Indeed, in certain embodiments, the one or more analysis modules 130 may be stored in the one or more storage media 134.

In certain embodiments, the one or more processors 132 may include a microprocessor, a microcontroller, a processor module or subsystem, a programmable integrated circuit, a programmable gate array, a digital signal processor (DSP), or another control or computing device. In certain embodiments, the one or more storage media 134 may be implemented as one or more non-transitory computer-readable or machine-readable storage media. In addition, in certain embodiments, the one or more storage media 134 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; or other types of storage devices. Such computer-readable or machine-readable storage medium or media are considered to be part of an article (or article of manufacture), which may refer to any manufactured single component or multiple components. In addition, in certain embodiments, the processor(s) 132 may be connected to a network interface 136 of the tool control system 38 to allow the tool control system 38 to communicate with the surface control system 42.

The specific embodiments described above have been illustrated by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A method, comprising:

flowing one or more fluids from a subterranean formation to flow through a downhole well tool disposed in a wellbore of a well during a deep transient testing (DTT) operation performed by the downhole well tool;

measuring data related to one or more properties of the one or more fluids using one or more downhole fluid analysis sensors disposed within the downhole well tool;

predicting, via a control system, a first predicted DTT surface gas rate based on the data measured related to the one or more properties of the one or more fluids;

determining, via the control system, a total number of moles of gas released at a surface of the well for each component of each fluid of the one or more fluids by dividing a mass of each component of each fluid of the one or more fluids by molecular weight of the one or more fluids; and determining, via the control system, a total volume of gas released at the surface of the well for each component of each fluid of the one or more fluids by multiplying the total number of moles for each component of each fluid of the one or more fluids by a molecular volume for each component of each fluid of the one or more fluids.

2. The method of claim 1, wherein the first predicted DTT surface gas rate comprises hydrocarbon content of the one or more fluids and gas emissions relating to the one or more fluids.

3. The method of claim 1, comprising:

detecting, via a gas meter of a mud-gas separator, surface measurement data relating to the one or more properties of the one or more fluids; and predicting, via the control system, a second predicted DTT surface gas rate based on the surface measurement data relating to the one or more properties of the one or more fluids.

4. The method of claim 1, wherein the one or more fluids comprise an oil-based mud.

5. The method of claim 1, wherein the one or more fluids comprise a water-based mud.

6. The method of claim 1, wherein the downhole well tool comprises the control system, and wherein predicting the first predicted DTT surface gas rate comprises:

determining, via the downhole well tool, each fluid of the one or more fluids flowing through the downhole well tool;

mapping, via the downhole well tool, a flowrate to a fluid density estimation or fluid density measurement for each fluid of the one or more fluids;

summing, via the downhole well tool, flowrates of similar fluids of the one or more fluids; and converting, via the downhole well tool, the summed flowrates from volume rates to mass rates by multiplying the volume rates to the fluid density estimation or fluid density measurement.

7. The method of claim 6, wherein the fluid density estimation or fluid density measurement comprises a direct measurement of fluid density via a fluid density sensor of the one or more downhole fluid analysis sensors.

8. The method of claim 6, wherein the fluid density estimation or fluid density measurement comprises an estimate of fluid density performed by the downhole well tool using one or more compositional measurements of the one or more fluids and a fluid model.

9. The method of claim 1, comprising determining, via the control system, a total volume of gas released at the surface of the well by summing the total volume of gas released at the surface of the well for each component of each fluid of the one or more fluids.

10. The method of claim 1, wherein the control system is a surface control system located at a surface of the well.

11. The method of claim 1, wherein the downhole well tool comprises the control system.

12. The method of claim 1, wherein the control system comprises a surface control system located at the surface of the well and a downhole control system disposed within the downhole well tool, and wherein the surface control system and the downhole control system are communicatively coupled.

13. The method of claim 1, further comprising:

flowing the one or more fluids to a surface of the well, wherein the one or more fluids comprise gas and mud; and separating the gas and the mud of the one or more fluids at the surface using a separator.

14. A method, comprising:

flowing one or more fluids from a subterranean formation to flow through a downhole well tool disposed in a wellbore of a well during a deep transient testing (DTT) operation performed by the downhole well tool;

measuring data related to one or more properties of the one or more fluids using one or more downhole fluid analysis sensors disposed within the downhole well tool;

predicting, via a control system, a first predicted DTT surface gas rate based on the data measured related to the one or more properties of the one or more fluids;

predicting, via the control system, a second predicted DTT surface gas rate based on measurement data detected by surface equipment of the well; and calculating, via the control system, a vapor fraction for each gaseous component of the one or more fluids, by comparing the first predicted DTT surface gas rate and the second predicted DTT surface gas rate.

15. The method of claim 14, wherein the control system is a surface control system located at a surface of the well.

16. The method of claim 14, wherein the downhole well tool comprises the control system.

17. A method, comprising:

flowing one or more fluids from a subterranean formation to flow through a downhole well tool disposed in a wellbore of a well during a deep transient testing (DTT) operation performed by the downhole well tool;

measuring data related to one or more properties of the one or more fluids using one or more downhole fluid analysis sensors disposed within the downhole well tool; and predicting, via a control system, a first predicted DTT surface gas rate based on the data measured related to the one or more properties of the one or more fluids, wherein the downhole well tool comprises the control system, and wherein predicting the first predicted DTT surface gas rate comprises:

determining, via the downhole well tool, a weight fraction for each fluid of the one or more fluids at a plurality of time steps; and determining, via the downhole well tool, a mass rate of each component of each fluid of the one or more fluids by multiplying the weight fraction for each component of each fluid of the one or more fluids by a total mass flowrate of the one or more fluids.

18. The method of claim 17, comprising:

determining, via the control system, a mass rate of gas released at a surface of the well by multiplying the mass rate of each component of each fluid of the one or more fluids with a vapor fraction of each component of each fluid of the one or more fluids; and determining, via the control system, a total mass of gas released at the surface of the well for each component of each fluid of the one or more fluids by summing the mass rate of gas released at the surface of the well over total time of the plurality of time steps.

19. The method of claim 17, comprising determining, via the control system, a total mass pumped into the wellbore of the well for each component of each fluid of the one or more fluids by summing the mass rate of each component of each fluid of the one or more fluids over total time of the plurality of time steps.

20. The method of claim 17, wherein the control system is a surface control system located at a surface of the well.

\* \* \* \* \*